US 12,409,324 B2

(12) United States Patent
Parker et al.

(10) Patent No.: US 12,409,324 B2
(45) Date of Patent: *Sep. 9, 2025

(54) SYSTEMS AND METHODS FOR DETECTING FAULTS AND/OR ADJUSTING ELECTRICAL THERAPY BASED ON IMPEDANCE CHANGES

(71) Applicant: Nevro Corp., Redwood City, CA (US)

(72) Inventors: Jon Parker, Portland, OR (US); Andre B. Walker, Monte Sereno, CA (US); Udai Singh, San Francisco, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/993,485

(22) Filed: Nov. 23, 2022

(65) Prior Publication Data

US 2023/0293889 A1    Sep. 21, 2023

Related U.S. Application Data

(63) Continuation of application No. 16/861,115, filed on Apr. 28, 2020, now abandoned, which is a
(Continued)

(51) Int. Cl.
A61N 1/36    (2006.01)

(52) U.S. Cl.
CPC ........ A61N 1/36142 (2013.01); A61N 1/3603 (2017.08); A61N 1/36071 (2013.01); A61N 1/36185 (2013.01)

(58) Field of Classification Search
CPC ............ A61N 1/36071; A61N 1/36142; A61N 1/36185; A61N 2001/083
See application file for complete search history.

(56) References Cited

U.S. PATENT DOCUMENTS

| 4,257,429 A | 3/1981 | Dickhudt et al. |
| 4,899,750 A | 2/1990 | Ekwall |

(Continued)

FOREIGN PATENT DOCUMENTS

| JP | 08503648 | 4/1996 |
| JP | 20020527159 | 8/2002 |

(Continued)

OTHER PUBLICATIONS

European Examination Report for European Patent Application No. 10730001.4, Applicant: Nevro Corporation, mailed Nov. 29, 2012. 4 pages.
(Continued)

Primary Examiner — Joseph M Dietrich

(57) ABSTRACT

System and methods for detecting impedance changes and for adjusting electrical therapy based on impedance changes are disclosed herein. A method in accordance with a particular embodiment includes applying a therapeutic, paresthesia-less electrical signal to a patient via a patient modulation system that includes a signal delivery device in electrical communication with a target neural population of the patient. The method can include monitoring on a periodic basis an impedance of an electrical circuit that includes the signal delivery device. The method can further include detecting a change in the impedance that indicates a fault and providing an indication that the fault exists.

20 Claims, 7 Drawing Sheets

Related U.S. Application Data continuation of application No. 15/728,399, filed on Oct. 9, 2017, now abandoned, which is a continuation of application No. 13/669,377, filed on Nov. 5, 2012, now Pat. No. 9,814,884.

(60) Provisional application No. 61/556,004, filed on Nov. 4, 2011.

(56) References Cited

U.S. PATENT DOCUMENTS

| | | | |
|---|---|---|---|
| 5,224,475 | A | 7/1993 | Berg et al. |
| 5,643,330 | A | 7/1997 | Holsheimer et al. |
| 5,782,884 | A | 7/1998 | Stotts et al. |
| 5,891,179 | A | 4/1999 | Er et al. |
| 5,938,690 | A | 8/1999 | Law |
| 6,052,624 | A | 4/2000 | Mann |
| 6,236,892 | B1 | 5/2001 | Feler |
| 6,319,241 | B1 | 11/2001 | King et al. |
| 6,393,325 | B1 | 5/2002 | Mann et al. |
| 6,461,357 | B1 | 10/2002 | Sharkey et al. |
| 6,622,048 | B1 | 9/2003 | Mann |
| 6,895,280 | B2 | 5/2005 | Meadows et al. |
| 6,909,917 | B2 | 6/2005 | Woods et al. |
| 6,947,792 | B2 | 9/2005 | Ben-Haim et al. |
| 6,978,171 | B2 | 12/2005 | Goetz et al. |
| 6,993,384 | B2 | 1/2006 | Bradley et al. |
| 7,020,523 | B1 | 3/2006 | Lu et al. |
| 7,024,246 | B2 | 4/2006 | Acosta et al. |
| 7,142,923 | B2 | 11/2006 | North et al. |
| 7,174,215 | B2 | 2/2007 | Bradley |
| 7,289,851 | B2 | 10/2007 | Gunderson et al. |
| 7,317,948 | B1 | 1/2008 | King et al. |
| 7,414,534 | B1 | 8/2008 | Kroll et al. |
| 7,444,181 | B2 | 10/2008 | Shi et al. |
| 7,447,545 | B2 | 11/2008 | Heruth et al. |
| 7,489,970 | B2 | 2/2009 | Lee et al. |
| 7,555,346 | B1 | 6/2009 | Woods et al. |
| 7,957,797 | B2 | 6/2011 | Bourget et al. |
| 7,957,809 | B2 | 6/2011 | Bourget et al. |
| 7,957,814 | B2 | 6/2011 | Goetz et al. |
| 8,016,776 | B2 | 9/2011 | Bourget et al. |
| 8,116,878 | B1 | 2/2012 | Palmer |
| 8,121,703 | B1 | 2/2012 | Palmer |
| 8,175,719 | B2 | 5/2012 | Shi et al. |
| 8,311,639 | B2 | 11/2012 | Parker et al. |
| 8,355,797 | B2 | 1/2013 | Caparso et al. |
| 8,457,759 | B2 | 6/2013 | Parker et al. |
| 8,498,710 | B2 | 7/2013 | Walker et al. |
| 8,626,312 | B2 | 1/2014 | King et al. |
| 8,712,533 | B2 | 4/2014 | Alataris et al. |
| 8,712,535 | B2 | 4/2014 | Walker et al. |
| 9,061,154 | B2 | 6/2015 | Parker et al. |
| 9,278,222 | B2 | 3/2016 | Thacker et al. |
| 9,295,840 | B1 | 3/2016 | Thacker et al. |
| 9,399,137 | B2 | 7/2016 | Parker et al. |
| 9,517,344 | B1 | 12/2016 | Bradley |
| 9,731,133 | B1 | 8/2017 | Thacker et al. |
| 9,776,006 | B2 | 10/2017 | Parker et al. |
| 9,814,884 | B2 * | 11/2017 | Parker .............. A61N 1/36142 |
| 9,895,538 | B1 | 2/2018 | Thacker |
| 9,937,348 | B1 | 4/2018 | Bradley |
| 10,086,204 | B2 | 10/2018 | Grill |
| 10,149,978 | B1 | 12/2018 | Park |
| 2002/0068930 | A1 | 6/2002 | Tasto et al. |
| 2003/0135248 | A1 | 7/2003 | Stypulkowski |
| 2003/0195582 | A1 | 10/2003 | Mann |
| 2004/0116978 | A1 | 6/2004 | Bradley |
| 2004/0172100 | A1 | 9/2004 | Humayun et al. |
| 2005/0060007 | A1 | 3/2005 | Goetz |
| 2005/0209645 | A1 | 9/2005 | Heruth et al. |
| 2006/0122620 | A1 | 6/2006 | Kim |
| 2006/0195159 | A1 | 8/2006 | Bradley et al. |
| 2006/0206118 | A1 | 9/2006 | Kim et al. |
| 2006/0224222 | A1 | 10/2006 | Bradley et al. |
| 2006/0253174 | A1 | 11/2006 | King |
| 2006/0259099 | A1 | 11/2006 | Goetz et al. |
| 2006/0265039 | A1 | 11/2006 | Bartic et al. |
| 2007/0043403 | A1 | 2/2007 | Blamey et al. |
| 2007/0073357 | A1 | 3/2007 | Rooney et al. |
| 2007/0135868 | A1 | 6/2007 | Shi et al. |
| 2007/0150029 | A1 | 6/2007 | Bourget et al. |
| 2007/0156207 | A1 | 7/2007 | Kothandaraman et al. |
| 2007/0179579 | A1 | 8/2007 | Feler et al. |
| 2007/0208394 | A1 | 9/2007 | King et al. |
| 2007/0213789 | A1 | 9/2007 | Nolan et al. |
| 2007/0249968 | A1 | 10/2007 | Miesel et al. |
| 2007/0265681 | A1 | 11/2007 | Gerber et al. |
| 2007/0276450 | A1 | 11/2007 | Meadows et al. |
| 2007/0276453 | A1 | 11/2007 | Hill et al. |
| 2008/0015657 | A1 | 1/2008 | Haefner |
| 2008/0046036 | A1 | 2/2008 | King et al. |
| 2008/0046052 | A1 | 2/2008 | Werder et al. |
| 2008/0064980 | A1 | 3/2008 | Lee et al. |
| 2008/0071325 | A1 | 3/2008 | Bradley |
| 2008/0154340 | A1 | 6/2008 | Goetz et al. |
| 2008/0183256 | A1 | 7/2008 | Keacher |
| 2008/0188909 | A1 | 8/2008 | Bradley |
| 2008/0215118 | A1 | 9/2008 | Goetz et al. |
| 2008/0215119 | A1 | 9/2008 | Woods et al. |
| 2008/0281381 | A1 | 11/2008 | Gerber et al. |
| 2008/0319511 | A1 | 12/2008 | Pless |
| 2009/0018617 | A1 | 1/2009 | Skelton et al. |
| 2009/0030476 | A1 | 1/2009 | Hargrove |
| 2009/0125079 | A1 | 5/2009 | Armstrong et al. |
| 2009/0149917 | A1 | 6/2009 | Whitehurst et al. |
| 2009/0204173 | A1 | 8/2009 | Fang et al. |
| 2009/0264956 | A1 | 10/2009 | Rise et al. |
| 2009/0264957 | A1 | 10/2009 | Giftakis et al. |
| 2009/0264967 | A1 | 10/2009 | Giftakis et al. |
| 2009/0281599 | A1 | 11/2009 | Thacker et al. |
| 2009/0306746 | A1 | 12/2009 | Blischak |
| 2009/0326608 | A1 | 12/2009 | Huynh et al. |
| 2010/0010432 | A1 | 1/2010 | Skelton |
| 2010/0010566 | A1 | 1/2010 | Thacker et al. |
| 2010/0049280 | A1 | 2/2010 | Goetz |
| 2010/0057162 | A1 | 3/2010 | Moffitt et al. |
| 2010/0069993 | A1 | 3/2010 | Greenspan |
| 2010/0121408 | A1 | 5/2010 | Imran et al. |
| 2010/0121409 | A1 | 5/2010 | Kothandaraman et al. |
| 2010/0137943 | A1 | 6/2010 | Zhu |
| 2010/0137944 | A1 | 6/2010 | Zhu |
| 2010/0144281 | A1 | 6/2010 | Kim et al. |
| 2010/0185256 | A1 | 7/2010 | Hulvershorn |
| 2010/0211135 | A1 | 8/2010 | Caparso et al. |
| 2010/0274312 | A1 | 10/2010 | Alataris et al. |
| 2010/0274314 | A1 | 10/2010 | Alataris et al. |
| 2010/0274317 | A1 | 10/2010 | Parker et al. |
| 2010/0274320 | A1 | 10/2010 | Torgerson |
| 2010/0277309 | A1 | 11/2010 | Anderson |
| 2010/0305631 | A1 | 12/2010 | Bradley et al. |
| 2010/0305660 | A1 | 12/2010 | Hegi et al. |
| 2011/0009927 | A1 | 1/2011 | Parker et al. |
| 2011/0040351 | A1 | 2/2011 | Butson et al. |
| 2011/0046697 | A1 | 2/2011 | Gerber et al. |
| 2011/0071593 | A1 | 3/2011 | Parker et al. |
| 2011/0093051 | A1 | 4/2011 | Davis et al. |
| 2011/0118661 | A1 | 5/2011 | Pless et al. |
| 2011/0184488 | A1 | 7/2011 | De Ridder et al. |
| 2011/0245708 | A1 | 10/2011 | Finkel et al. |
| 2011/0301679 | A1 | 12/2011 | Rezai |
| 2012/0083857 | A1 | 4/2012 | Bradley et al. |
| 2012/0116476 | A1 | 5/2012 | Kothandaraman |
| 2012/0130448 | A1 | 5/2012 | Woods et al. |
| 2012/0172946 | A1 | 7/2012 | Alataris |
| 2012/0253422 | A1 | 10/2012 | Thacker et al. |
| 2012/0265268 | A1 | 10/2012 | Blum et al. |
| 2012/0265271 | A1 | 10/2012 | Goetz |
| 2013/0023950 | A1 | 1/2013 | Gauthier |
| 2013/0060302 | A1 | 3/2013 | Polefko et al. |
| 2013/0066411 | A1 | 3/2013 | Thacker et al. |
| 2013/0116752 | A1 | 5/2013 | Parker et al. |
| 2013/0138179 | A1 | 5/2013 | DeRidder |
| 2013/0261694 | A1 | 10/2013 | Caparso et al. |

(56) References Cited

U.S. PATENT DOCUMENTS

| | | |
|---|---|---|
| 2013/0261697 A1 | 10/2013 | Parker |
| 2013/0282078 A1 | 10/2013 | Wacnik |
| 2013/0289667 A1 | 10/2013 | Wacnik et al. |
| 2013/0310892 A1 | 11/2013 | Parker et al. |
| 2014/0067016 A1 | 3/2014 | Kaula |
| 2014/0081349 A1 | 3/2014 | Lee et al. |
| 2014/0081350 A1 | 3/2014 | Zhu |
| 2014/0330338 A1 | 11/2014 | Walker et al. |
| 2014/0343622 A1 | 11/2014 | Alataris |
| 2015/0005842 A1 | 1/2015 | Lee |
| 2015/0039047 A1 | 2/2015 | Parker |
| 2015/0039048 A1 | 2/2015 | Woods |
| 2015/0151125 A1 | 6/2015 | Zhu et al. |
| 2015/0165209 A1 | 6/2015 | Grandhe et al. |
| 2015/0217113 A1 | 8/2015 | Walker et al. |
| 2015/0321000 A1 | 11/2015 | Rosenbluth |
| 2016/0158551 A1 | 6/2016 | Kent |
| 2018/0056072 A1 | 3/2018 | Parker |
| 2020/0353263 A1 | 11/2020 | Parker |

FOREIGN PATENT DOCUMENTS

| | | |
|---|---|---|
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-2006119046 A1 | 11/2006 |
| WO | WO-2007149018 A1 | 12/2007 |
| WO | WO-2008142402 A1 | 11/2008 |

OTHER PUBLICATIONS

Keuchmann C et al., "853 Could Automatic Position Adaptive Stimulation be Useful in Spinal Cord Stimulation," Abstract, Medtronic, Inc., undated, 1 page.

Hayt et al., "Engine Circuit Analysis," McGraw-Hill Book Company, Fourth Edition, 1986, 18 pages.

Extended European Search Report for European Patent Application No. 18173990.5, Applicant: Nevro Corporation, mailed Dec. 14, 2018, 6 pages.

* cited by examiner

SYSTEMS AND METHODS FOR DETECTING FAULTS AND/OR ADJUSTING ELECTRICAL THERAPY BASED ON IMPEDANCE CHANGES

CROSS-REFERENCE TO RELATED APPLICATIONS

The present application is a continuation of U.S. patent application Ser. No. 16/861,115, filed on Apr. 28, 2020, which is a continuation of U.S. patent application Ser. No. 15/728,399, filed Oct. 9, 2017, which is a continuation of U.S. patent application Ser. No. 13/669,377, filed Nov. 5, 2012, now issued as U.S. Pat. No. 9,814,884, which claims priority to U.S. Provisional Application No. 61/556,004, filed on Nov. 4, 2011 and are incorporated herein by reference. To the extent the foregoing application and/or any other materials incorporated herein by reference conflict with the present disclosure, the present disclosure controls.

TECHNICAL FIELD

The present disclosure is directed generally to systems and methods for detecting faults and/or adjusting electrical therapy provided to patients, based on changes in the impedance of circuits providing the therapy, including changes detected while applying therapeutic electrical signals to a patient's spinal cord.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator (sometimes referred to as an "implantable pulse generator" or "IPG") and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the signal generator applies electrical signals to the electrodes, which in turn modify the function of the patient's nervous system, such as by altering the patient's responsiveness to sensory stimuli and/or altering the patient's motor-circuit output. In pain treatment, the pulse generator applies electrical signals to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. As used herein, unless explicitly stated otherwise, the terms "pulses" and "signals" are used interchangeably to include any waveform shapes, whether continuous or discontinuous, including but not limited to sinusoidal or non-sinusoidal waves such as square waves, triangle waves, sawtooth waves, etc.

One problem associated with existing stimulation systems is that aspects of the systems and/or the interactions between the systems and the patient may change over time. For example, the impedance of a stimulation circuit (which includes implanted electrodes and the patient's tissue) can change as scar tissue forms at the implant site and/or if the lead moves within the patient, and/or if the lead becomes disconnected or undergoes other changes. As the circuit impedance changes, the strength of the applied signal changes, which can reduce the efficacy of the signal and/or create patient discomfort. Accordingly, there remains a need for improved techniques and systems for addressing patient pain in a manner that is effective and comfortable over an extended period of time.

DETAILED DESCRIPTION

Figure 1:
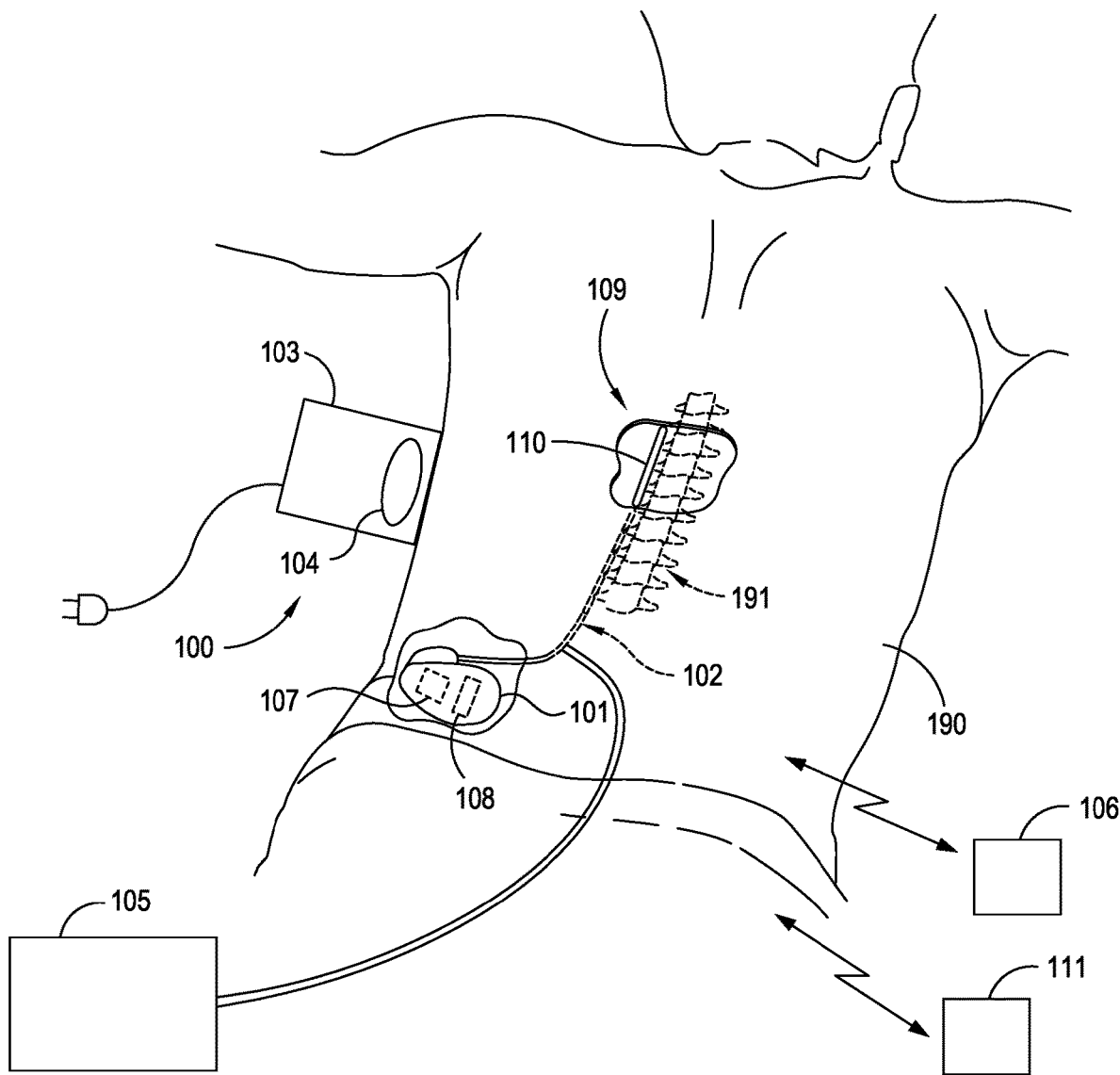
FIG. 1 is a partially schematic illustration of an implantable spinal cord stimulation system positioned at the spine to deliver therapeutic signals in accordance with an embodiment of the present disclosure.

The present disclosure is directed generally to systems and methods for adjusting electrical therapy parameters based on detected changes in the impedance of an electrical circuit that provides the electrical therapy. Specific details of certain embodiments of the disclosure are described below with reference to adjusting therapy parameters for spinal cord modulators, which may be used to treat chronic pain. However, the disclosed systems and methods may be used in the context of other modulators and/or other patient conditions. Accordingly, some embodiments can have configurations, components, or procedures different than those described in this section, and other embodiments may eliminate particular components or procedures. The invention may have other embodiments with additional elements, and/or may have other embodiments without several of the features shown and described below with reference to FIGS. 1-6.

Overview

During the course of a typical spinal cord modulation therapy regimen and/or a trial period leading up to the therapy regimen, the impedance of the electrical circuit that provides electrical therapy to the patient may change for any variety of reasons. For example, if the patient changes position and the implanted lead carrying the therapy electrodes shifts, the circuit impedance may change because the electrodes are now adjacent to tissue and/or fluid having different impedance characteristics. If the circuit impedance changes suddenly, the patient may experience a sudden change in the applied current and/or voltage, potentially causing patient discomfort. In other cases, scar tissue may be present at implant and/or build up on the electrodes, decreasing the efficacy with which the electrical signals are provided to the patient. In still other cases, individual electrodes may short together, or the lead may become disconnected or partially disconnected from the signal generator, creating one or more open circuits that reduce or eliminate the efficacy of the therapy. In any of these instances, certain aspects of the following disclosure can automatically detect changes in circuit impedance and automatically respond to the changes in a manner that improves patient comfort and/or improves the efficacy of the therapy.

In systems that do not produce paresthesia, patients can experience a lag between a loss of signal or a decrease in signal strength and the recurrence of pain. This lag can result in a delay between the occurrence of a fault in the system and the time at which a patient becomes aware of the fault. Consequently, without awareness of the fault, the patient may fail to correct and/or compensate for the fault before the pain returns. Accordingly, there is a need for techniques and systems that can monitor for and detect a loss of connection or an impedance change and provide notification and/or signal changes to adapt to the loss of connection or impedance change.

A method in accordance with a particular embodiment of the disclosure includes applying a therapeutic signal to the patient via an external stimulator or trial modulator that includes a signal delivery device in electrical communication with a target neural population of the patient. The electrical signal is delivered in accordance with one or more signal delivery parameters. The method can further include detecting a change in the impedance of an electrical circuit that includes the signal delivery device, using the external trial modulator of the patient modulation system. The detection of the change in impedance can include a periodic impedance check (e.g., at a preset periodic interval) that uses the therapeutic signal and/or a non-therapeutic signal. Accordingly, aspects of this embodiment include automatically detecting a change in impedance during a therapy regimen that does not produce patient paresthesia or other sensory or motor effects, the absence of which would signal to the patient that a fault and/or impedance change has occurred.

A method in accordance with another embodiment of the disclosure includes applying a therapeutic electrical signal to a patient via an implanted portion of a patient modulation system that includes a signal delivery device in electrical communication with a target neural population of the patient. The method can include detecting a change in the impedance of an electrical circuit that includes the signal delivery device, using the implanted portion of the patient modulation system. Based at least in part on the detected impedance change, the method can still further include automatically adjusting the value of the signal delivery parameter(s) without human intervention. Accordingly, the process of detecting impedance changes and responding to the detected changes can be performed autonomously by the implanted portion of the patient modulation system.

A method in accordance with yet another aspect of the disclosure includes automatically identifying changes in the impedance of an electrical circuit that provides therapy to the patient, as a function of time. Based at least upon identifying the changes in impedance as a function of time, the method can further include predicting a future value of the impedance and automatically performing a task based on the predicted future value. Representative tasks include predicting a lead failure, confirming that an identified impedance trend conforms with an expected trend, and/or providing notice to a patient or practitioner of a predicted change in impedance value.

Representative Systems and Methods

Figure 1B:
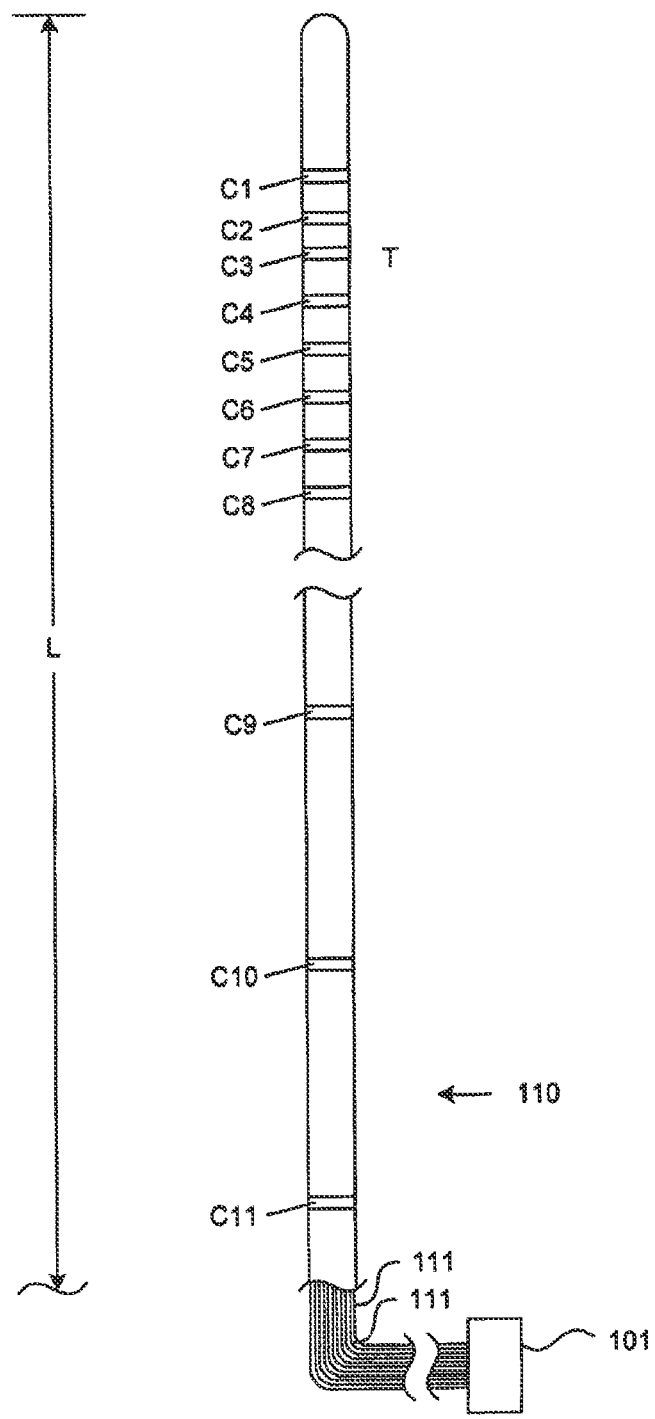
FIG. 1B is a partially schematic illustration of a lead having electrode contacts that form elements of one or more therapy circuits having impedances that are detected in accordance with methods of the present disclosure.

In the following discussion, FIGS. 1 and 1B illustrate a representative implementation of a system implanted in the patient's spinal cord region, and FIGS. 2-6 illustrate representative methods and associated circuits and waveforms for detecting impedance changes and responding to the detected changes. FIG. 1 schematically illustrates a representative treatment system 100 for providing relief from chronic pain and/or other conditions, arranged relative to the general anatomy of a patient's spinal cord 191. The system 100 can include a signal generator 101 (e.g., a pulse generator), which may be implanted subcutaneously within a patient 190 and coupled to a signal delivery element 109. In a representative example, the signal delivery element 109 includes a lead or lead body 110 that carries features or elements for delivering therapy to the patient 190 after implantation. The signal generator 101 can be connected directly to the lead body 110, or it can be coupled to the lead body 110 via a communication link 102 (e.g., an extension). As used herein, the terms lead and lead body include any of a number of suitable substrates and/or support members that carry devices for providing therapy signals to the patient 190. For example, the lead body 110 can include one or more electrodes or electrical contacts that direct electrical signals into the patient's tissue, such as to provide for patient relief. In other embodiments, the signal delivery element 109 can include devices other than a lead body (e.g., a paddle) that also direct electrical signals and/or other types of signals to the patient 190.

The signal generator 101 can transmit signals (e.g., electrical signals or therapy signals) to the signal delivery element 109 that up-regulate (e.g., stimulate or excite) and/or down-regulate (e.g., block or suppress) target nerves. As used herein, and unless otherwise noted, to "modulate," or provide "modulation" to the target nerves refers generally to having either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processors 107, memories 108 and/or input/output devices. Accordingly, the process of determining impedance and taking follow-up action can be performed by computer-executable instructions contained on computer-readable media, e.g., the processor(s) 107 and/or memory(s) 108. The signal generator 101 can include multiple portions, elements, and/or subsystems (e.g., for directing signals in accordance with multiple signal delivery parameters), housed in a single housing, as shown in FIG. 1, or in multiple housings. In any of these embodiments, the signal generator 101 and/or other implanted components of the system 100 can include elements for detecting and responding to impedance changes.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In some cases, an external stimulator 105 (e.g., a trial modulator) can be coupled to the signal delivery element 109 during an initial implant procedure, prior to implanting the signal generator 101. For example, a practitioner (e.g., a physician and/or a company representative) can use the external stimulator 105 to vary the modulation parameters provided to the signal delivery element 109 in real time, and select optimal or particularly efficacious parameters. During this process, the practitioner can also vary the position of the signal delivery element 109. After the position of the signal delivery element 109 and appropriate signal delivery parameters are established using the external stimulator 105, the patient 190 can receive therapy via signals generated by the external stimulator 105, generally for a limited period of time. In a representative application, the patient 190 receives such therapy for one week. During this period, the external stimulator 105 can monitor the impedance and continuity of an electrical circuit that includes the external stimulator 105 and the signal delivery element 109. Assuming the trial therapy is effective or shows the promise of being effective, the practitioner then replaces the external stimulator 105 with the implanted signal generator 101, and programs the signal generator 101 with parameters selected based on the experience gained during the trial period. Optionally, the practitioner can also replace the signal delivery element 109. Once the implantable signal generator 101 has been positioned within the patient 190, the signal delivery parameters provided by the signal generator 101 can still be updated remotely via a wireless physician's programmer (e.g., a physician's laptop, physician's remote, etc.) 111 and/or a wireless patient programmer 106 (e.g., a patient's laptop, patient's remote, etc.). Generally, the patient 190 has control over fewer parameters than does the practitioner. For example, the capability of the patient programmer 106 may be limited to starting and/or stopping the signal generator 101, and/or adjusting modulation amplitude.

In any of the foregoing embodiments, the parameters in accordance with which the signal generator 101 provides signals can be modulated during portions of the therapy regimen. For example, the frequency, amplitude, pulse width, duty cycle, and/or signal delivery location can be modulated in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Such parameter changes can also be implemented automatically to account for detected impedance changes.

For example, as described above, the signal can be delivered at a frequency of from about 1.5 kHz to about 100 kHz, and in particular embodiments, from about 1.5 KHz to about 50 KHz. In more particular embodiments, the signal can be provided at frequencies of from about 3 kHz to about 20 kHz, or from about 3 kHz to about 15 kHz, or from about 5 kHz to about 15 kHz, or from about 3 kHz to about 10 KHz. The amplitude of the signal can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, filed Nov. 4, 2008, and incorporated herein by reference. In particular embodiments, the signal amplitude refers to the electrical current level, e.g., for current-controlled systems. In other embodiments, the signal amplitude can refer to the electrical voltage level, e.g., for voltage-controlled systems. The pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

FIG. 1B illustrates a representative lead 110 that can be connected to the signal generator 101. The lead 110 can have any suitable number of contacts C positioned along its length L for delivering electrical therapy to the patient. For purposes of illustration, 11 contacts C, identified individually as contacts C1, C2 . . . C11 are shown in FIG. 1B. In operation, one or more of the contacts C is cathodic and another one or more of the contacts C is anodic. The contacts C can be individually addressable so that any contact C or combination of contacts C can operate as a cathode, and any contact C or combination of contacts C can operate as an anode. The contacts C can be electrically grouped in any of a wide variety of combinations, and individual contacts C can perform different functions (e.g., cathodic functions and/or anodic functions) at different times during the course of a therapy regimen. In any of these embodiments, each contact C may be coupled with a corresponding conductor 111 to the signal generator 101. The conductors 111 may have one or more connection points along their lengths (e.g., at a junction with the signal generator 101, and optionally at a junction with an extension). Accordingly, the circuit for a given pair of contacts C includes the contacts C, the patient tissue T between the contacts, the individual conductors 111, connection points along the conductors 111, and connection points between the conductors 111 and the signal generator 101. As discussed below, aspects of the present disclosure are directed to detecting changes in the overall circuit impedance that may result from changes at any of a variety of points along the circuit, and providing an appropriate response.

Figure 2:
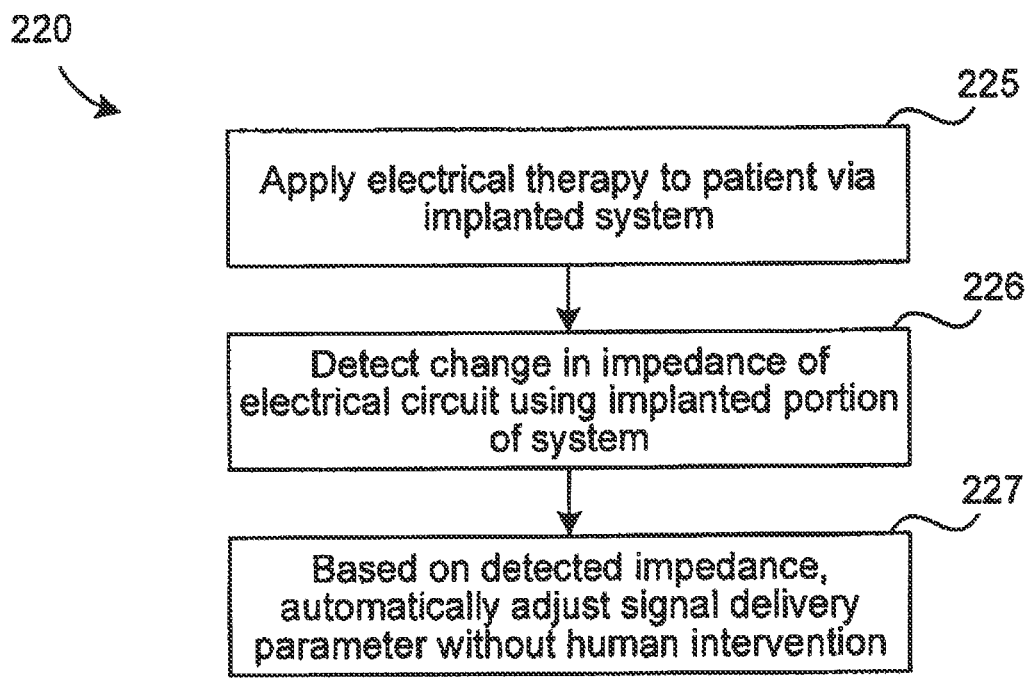
FIG. 2 is a flow diagram illustrating a process for adjusting electrical therapy parameters in response to detected changes in therapeutic circuit impedance.
Figure 3:
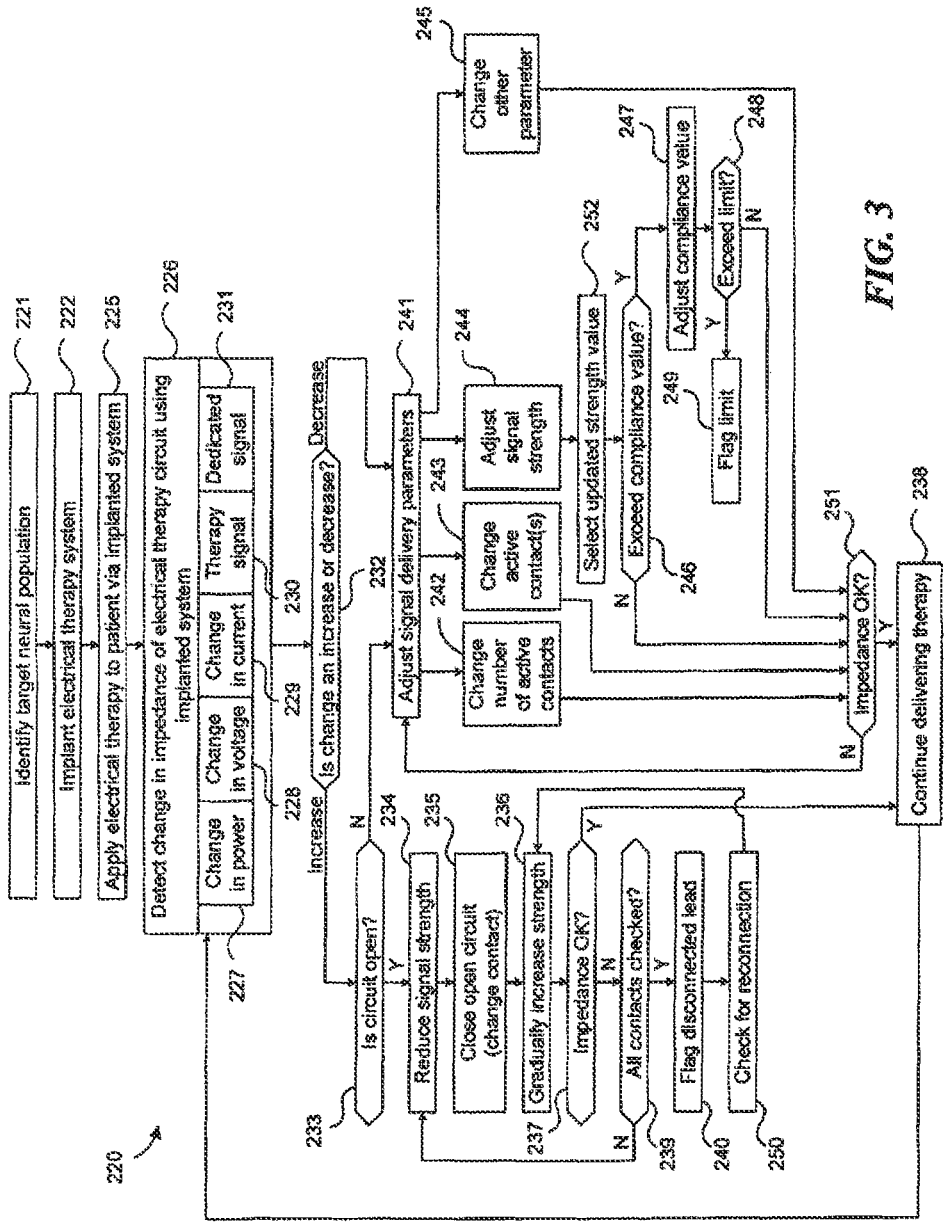
FIG. 3 is a flow diagram illustrating further details of processes for detecting and responding to changes in therapy circuit impedance, in accordance with further embodiments of the disclosure.

FIG. 2 illustrates an overall process 220 in accordance with a particular embodiment of the disclosure. The process 220 includes applying electrical therapy to a patient via an implanted or partially implanted system (process portion 225). The partially implanted system can include an implanted signal delivery device and an external programmer or trial modulator similar to the external programmer 105 (FIG. 1). During the course of the therapy and/or the trial therapy, the process 220 can further include detecting a change in the impedance of an electrical circuit that provides the therapy and/or the trial therapy, using the implanted portion of the system (process portion 226). Based on the detected impedance change, the process 220 can still further include automatically adjusting signal delivery parameters in accordance with which the therapy is provided, without human intervention (process portion 227). The signal delivery parameters can include signal strength, the location and/or number of electrical contacts delivering therapy to the patient, and/or other parameters. FIG. 3 describes further aspects of particular embodiments of the foregoing process.

FIG. 3 is a block diagram illustrating in further detail aspects of the overall process 220 described above with reference to FIG. 2. Process portion 221 includes identifying a target neural population. For example, process portion 221 can include identifying one or more neural populations at particular vertebral locations along the patient's spine. Process portion 222 includes implanting an electrical therapy system, for example, implanting the signal delivery element 109 and the signal generator 101 described above with reference to FIGS. 1 and 1B. As discussed above with reference to FIG. 1B, the electrical therapy system includes at least one electrical therapy circuit which has associated with it an initial impedance value. In process portion 225, electrical therapy is applied to the patient via the implanted or partially implanted system with the initial impedance value. The impedance value may change over time, which is detected in process portion 226. Accordingly, the overall process can include automatically checking the impedance on a preset, periodic basis. In other embodiments, the system can check the impedance on an on-demand basis, e.g., in response to a patient or practitioner initiated inquiry, in addition to or in lieu of automatically checking the impedance.

The electrical therapy signals are typically time-varying signals (e.g., pulses), and the associated circuit can include capacitive and/or resistive elements. Accordingly, the detected impedance can include capacitive and/or resistive components. In particular embodiments, the system can distinguish between resistive and capacitive components of the overall impedance, and use this information to select the appropriate signal delivery parameter to vary. For example, if the impedance change is primarily capacitive, changing the signal delivery frequency may have a greater effect than if the impedance change is primarily resistive.

The change in impedance of the electrical circuit can be detected by detecting a change in power applied to the circuit (process portion 227), a change in voltage at one or more points along the circuit (process portion 228), a change in current passing through the circuit (process portion 229), and/or changes in other values. In a particular embodiment (process portion 230), the impedance of the electrical therapy circuit is detected while the therapy signal is delivered, for example, by sampling the therapy signal itself. In other embodiments, a dedicated electrical signal can be applied to the electrical therapy circuit and sampled, so as to detect impedance and/or impedance changes, independent of the therapy signal (process portion 231). Accordingly, this arrangement can be used to detect impedance and/or impedance changes of a therapy circuit without the need for the therapy signal to be active on the circuit at that time.

In any of the foregoing embodiments, the process 220 can include different steps depending upon the magnitude and/or direction of the impedance change. In a particular embodiment, process portion 232 can include determining whether the impedance change is an increase or a decrease. If the change is an increase, process portion 233 can include determining whether the circuit is open. An open circuit can be indicated by an infinite impedance, or by an impedance or impedance increase that exceeds a suitable threshold value.

Process portions 234-240 may be performed if, in process portion 233, it is determined that the electrical therapy circuit is open. For example, process portion 234 can include reducing the signal strength (e.g., the applied current and/or voltage) prior to closing or attempting to close the open circuit (process portion 235). In particular embodiments, process portion 234 can include reducing the signal strength to zero, or to a suitable non-zero value such that when the circuit is later closed, the patient does not receive an uncomfortable sensation. Process portion 235 can, for example, include changing one or more of the contacts (e.g., those shown in FIG. 1B) that form a portion of the electrical therapy circuit. This change can be achieved by opening and closing appropriate switches at the signal generator 101 or at the external programmer 105. Once the change has been made, process portion 236 can include gradually increasing the strength of the signal applied to the therapy circuit. By first reducing the signal strength (process portion 234) and then gradually increasing the signal strength after the change in the circuit has been made (process portion 236), the process 220 can avoid subjecting the patient to a sudden increase in the applied signal, which may cause patient discomfort.

Once the signal strength has been increased, process portion 237 can include checking the impedance to determine whether it has returned to its original level, or has otherwise achieved an acceptable level. This process can include checking the power, voltage, and/or current, as described above with reference to process portions 227-229. If the impedance is at an acceptable level, process portion 238 includes continuing to deliver the therapy. In addition, the patient and/or practitioner can be notified that a change has been made to account for the detected increase in impedance. The notification can take any of a variety of suitable forms, including a vibratory signal, and/or an internally stored signal that is downloaded external to the patient during a battery recharge operation or diagnostic operation. If the change did not result in an adequately improved impedance level, then in process portion 239, the system checks to determine whether all the contacts of the implanted lead have been checked. If not, the process returns to process portion 234 and a different contact is placed in the circuit. If, after all of the contacts have been checked and determined to form an open circuit, this can indicate that the lead is disconnected, which is flagged for the user and/or practitioner in process portion 240, using any suitable notification technique. In process portion 250, the system checks for lead reconnection, e.g., by rechecking all contacts for an open circuit. Once the lead has been reconnected, the system returns to process portion 236 so as to gradually increase signal strength.

If in process portions 232 and 233, the system determines that the impedance has decreased, or has increased but not so much as to indicate an open circuit, then in process portion 241, the signal delivery parameters are adjusted in an autonomous manner to bring the impedance values to acceptable levels. Process portion 241 can in turn include changing any of a variety of signal delivery parameters as identified by process portions 242-245. For example, process portion 242 can include changing the number of active contacts in the electrical therapy circuit. The number of active contacts may be increased in particular embodiments if the circuit impedance increases (e.g., to provide parallel electrical paths), and may be decreased in other embodiments if the impedance decreases. In a particular example, the patient may change position or the lead may change position relative to the patient such that the circuit impedance increases because the active contacts are now positioned adjacent to a portion of the patient tissue having a higher impedance. By increasing the number of active contacts, the resulting circuit can include portions of the patient tissue having a lower impedance. Of course, when such a change is made, it is made so that the resulting therapy is still applied to the appropriate portion of the patient tissue, even though the range over which the active contacts are positioned and may now be expanded. For example, only a subset of the contacts shown in FIG. 1B may be used and/or available for such a change, so as to avoid directing the therapy signal too far from the originally intended neural population.

In other embodiments, the system can automatically detect a decrease in the impedance of the therapy circuit. For example, if the lead shifts to a location within the patient that results in a lowered impedance, the system can automatically detect this occurrence. One such example is if the lead shifts from an initial position so as to be in closer proximity to cerebral spinal fluid, which has a relatively low impedance. In such instances, the number of electrical contacts applying the therapy may be decreased. In any of the foregoing embodiments once the responsive change has been made, the process can continue with process portion 251, which includes determining whether the new circuit produces a target impedance value. If so, then in process portion 238, the system delivers additional therapy. In addition, the system can notify the patient and/or practitioner of the update. If the change has not produced a target impedance value, the process returns to process portion 241. At that point, process portion 242 can be re-executed using a different combination of electrodes, or any of process portions 243-245 can be executed.

Process portion 243 includes changing the contacts that are active, for example, without increasing or decreasing the number of active contacts. In a particular example, process portion 243 can include substituting one contact for another. The substituted contact can be an anodic contact or a cathodic contact, and in some embodiments, both anodic and cathodic contacts can be changed. Once the contacts have been changed, the impedance is checked (process portion 251) and the process continues in a manner generally similar to that discussed above.

Process portion 244 includes adjusting the signal strength (increasing or decreasing the strength) in response to an indication that an impedance has changed. The signal strength can correspond to a voltage level, a current level, and/or a power level. Process portion 244 can in turn include selecting an updated strength value (e.g., an updated voltage value or current value) as shown in process portion 252, and then determining whether the updated strength value exceeds a predetermined compliance value (process portion 246). For example, a typical constant current source provides signals at a constant current by modulating the applied voltage, but keeping the applied voltage below a predetermined compliance voltage value, e.g., a programmed compliance voltage. If the selected updated strength value does not result in the compliance value being exceeded, then the impedance can optionally be rechecked in process portion 251 and the system can then deliver additional therapy (process portion 238). The impedance check at process portion 251 may be optional in this case because changing the signal strength may not change impedance.

If, in process portion 246 it is determined that the compliance value is exceeded by the selected updated strength value, then in process portion 247, the compliance value is adjusted. As discussed above, a constant current source automatically adjusts the applied voltage to account for at least some changes in the circuit impedance, so as to effectively produce a constant current. If the circuit impedance increases beyond a level that can be accommodated by a voltage change that remains within the maximum compliance voltage value, the compliance voltage can be adjusted, within preset limits that are established to provide for patient safety and comfort. Accordingly, in process portion 248, the system determines whether such a preset limit on the degree to which the compliance voltage can be adjusted has been exceeded. If it has not, then the impedance can optionally be checked (process portion 251) and the therapy delivered to the patient (process portion 238). If the necessary compliance value exceeds the preset limit, then in process portion 249, the user and/or the practitioner can be notified that the recommended signal strength is not available without exceeding preset limits on the amount by which the compliance value can be changed. In addition to or in lieu of providing such notification, the process can automatically revert to one of the other available methods for adjusting the signal delivery parameters, including process portion 242 (changing the number of active contacts), process portion 243 (changing which contacts are active), and/or process portion 245 (changing other parameters). The other parameters that may be changed can include, but are not limited to, frequency, pulse width, and/or duty cycle.

In some embodiments, the compliance voltage value is increased, e.g., to account for an increased circuit impedance. In other embodiments, the compliance voltage value is decreased, e.g., in response to an impedance reduction. In any of the foregoing embodiments, it can be advantageous to keep the compliance value as low as possible, while still providing signals at an effective signal strength, so as to reduce the power consumed by the system. Accordingly, the system can automatically adjust the compliance margin (e.g., the difference between the compliance voltage and actual delivered voltage). For example, the system can automatically set the compliance margin to be a fixed level (in volts or millivolts) above the actual delivered voltage (e.g., the updated strength value). In other embodiments, the compliance margin can be a fixed percentage of the updated strength value. In still further embodiments, the compliance margin can vary, and can be automatically adjusted based on the range of requested strength perturbations, e.g., the degree to which the updated strength values deviate from the strength value being applied at that time. If the range is wide, the compliance margin can be correspondingly wide to avoid having to repeatedly adjust the compliance value. If the range is narrow, the compliance margin can be correspondingly narrow to reduce power consumption. Accordingly, in particular embodiments, the system can automatically track the foregoing perturbations and automatically adjust the compliance margin.

In particular instances, the foregoing arrangement can track the gradual reduction in the range of impedance perturbations that result when a newly implanted lead becomes "scarred in." The system can also track increases in the range of impedance perturbations if the scar tissue continues to build up in a manner that requires frequent upward adjustments in signal strength, and/or if the lead and/or patient undergo other changes that affect circuit impedance.

The systems and methods described above can operate in accordance with a variety of different modes. For example, during a first mode of operation, the system can check the impedance of one or more circuits that include only active therapy contacts. If, during the first mode of operation, the system identifies an impedance change in association with the active contact(s), it can then check the impedance of inactive contacts during a second mode of operation. Based on the impedance measurements obtained during the second mode, the system can automatically change which contacts are active and which are inactive. This arrangement can reduce the time and power required to perform an impedance check because inactive contacts are checked only when an impedance change is identified in association with one or more active contacts.

One feature of several embodiments described herein is that the system 100 can automatically identify changes in impedance via an implanted portion of the system, and automatically take appropriate action without patient or practitioner intervention. An advantage of this feature is that the system need not rely on external analysis and/or diagnostics, and accordingly can implement the action more quickly and/or more conveniently.

Another feature of several embodiments described herein is that the system 100 can identify a fault, e.g., an open circuit or another fault that results in a detectable impedance change, and provide an indication or notification to the patient and/or practitioner. In systems that do not produce paresthesia, the delayed onset of pain can allow the patient and/or the practitioner and/or the system itself to be alerted and and/or correct and/or compensate for the fault prior to the patient experiencing the resulting pain and/or other sensory indication of the fault. The system can also automatically check to see that the fault has been corrected, e.g., before restarting delivery of the therapeutic signal. The notification can include any of a variety of suitable signals, e.g., a vibratory signal, a signal that is internally generated and then used internally and/or transmitted or downloaded external to the patient, and/or an externally generated signal.

Yet another feature of several of the embodiments described herein is that the system 100 can automatically identify an open circuit (e.g., a disconnected lead) and then gradually increase the strength of the applied therapy signal once the open circuit has been closed. An advantage of this feature is that it can reduce or eliminate the likelihood for the patient to feel a sudden shock or discomfort, which may otherwise result when the therapy signal is suddenly re-applied at the target strength value.

Still another feature of several of the embodiments described herein is that the system 100 can automatically adjust a preset compliance level (e.g., a voltage or current) to account for impedance changes. While increasing the compliance level may reduce overall system efficiency (e.g., may result in an increased power consumption), the patient can receive dynamically updated and effective therapy in a short period of time. This arrangement can allow the patient to continue receiving effective therapy until the power source is recharged or replaced, as opposed to potentially requiring that the patient undergo an in-office procedure to address the source of the impedance change (e.g., lead movement or scar tissue).

Yet another feature of several of the disclosed embodiments is that the system can detect impedance changes while the patient is receiving therapy. Accordingly, the patient's therapy need not be interrupted to provide this function. In addition, the system can not only check the impedance of the lead contacts applying therapy at a given time, but also other contacts. Accordingly, the system can readily identify alternate contacts that may be substituted for or provided in addition to the currently active contacts, to address changes in impedance. In addition, this arrangement allows the system to rapidly identify conditions that may affect contacts other than just the currently active contacts. Such conditions include a disconnected lead.

Figure 4A:
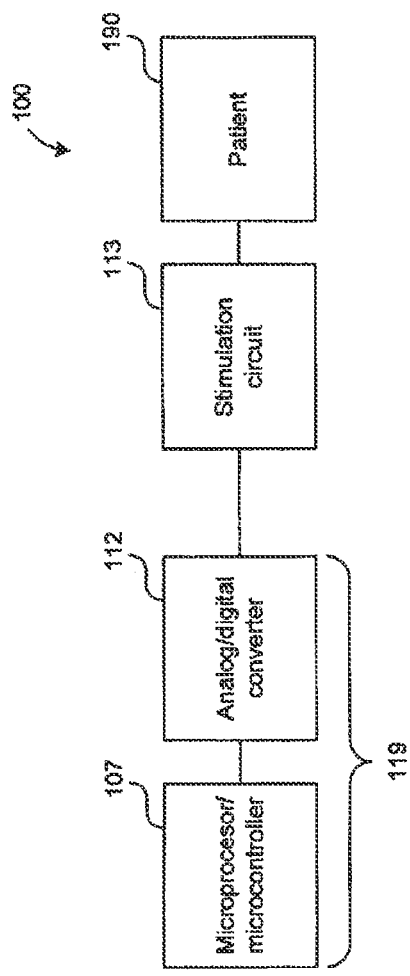
FIG. 4A is a schematic illustration of a representative detection system in accordance with an embodiment of the disclosure.

FIG. 4A is a schematic illustration of portions of the system 100 used for impedance detection in accordance with an embodiment of the disclosure. The system 100 can include an impedance detector 119 that in turn includes a microcontroller or microprocessor 107 that is coupled to an analog-to-digital (A/D) converter 112. The A/D converter 112 is coupled to a modulation circuit 113 that includes one or more electrical contacts, and is implanted in the patient 190. Accordingly, the A/D converter 112 converts analog signals (e.g., voltage and/or current levels) to digital values, which are analyzed by the microprocessor 107 to identify impedance changes.

Figure 4B:
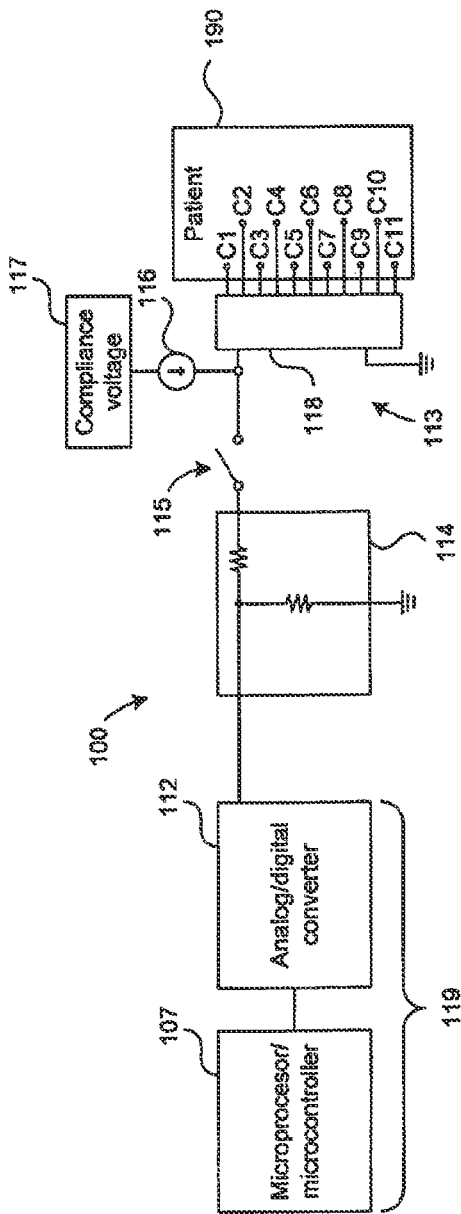
FIG. 4B is a schematic illustration of a representative circuit for detecting impedance changes in accordance with another embodiment of the disclosure.

FIG. 4B is a representative circuit diagram of an embodiment of the system 100 described above with reference to FIGS. 1 and 4A. In this particular embodiment, the A/D converter 112 is connected to a voltage divider 114, which is in turn selectively couplable to the modulation circuit 113 via an enable measurement switch 115. In other embodiments, the voltage divider 114 can be replaced with other suitable elements, for example, an amplifier. In any of these embodiments, the modulation circuit 113 can include a constant current source 116 that receives a compliance voltage input 117, which can in turn be initially preset and then optionally adjusted within further preset limits, as discussed above. The constant current source 116 can be coupled to a contact selector 118, which is in turn connected to the contacts C1, C2 . . . C11 positioned at the patient 190. The contact selector 118 can include any of a wide variety of suitable switching devices used to select one or more of the contacts C1-C11 for applying therapy to the patient, and/or for impedance detection. The circuit can include an H-bridge or other suitable element to selectively reverse the current direction for one or more combinations of contacts C. In other embodiments, the system 100 can include other suitable arrangements, for example, a constant voltage source rather than a constant current source, a current sink in addition to the constant current source, and/or other suitable arrangements known to those of ordinary skill in the relevant art.

In any of the foregoing embodiments, the detector 119 will typically detect the impedance of a circuit that includes at least two contacts, e.g., C1 and C2. If the circuit impedance increases beyond a preset threshold, the system can automatically step through the remaining contacts, e.g., C1 in combination with C3, C1 in combination with C4, and so on. This sequential process can be completed for any combination of contacts that may be suitable for continuing the patient therapy. In any of these cases, however, the impedance of the tested circuit will include the impedances of all the contacts in the circuit. Accordingly, the microprocessor 107 can include one or more of a variety of provisions for isolating impedance changes to a particular contact or contacts. For example, in one case, a nominal impedance can be assigned to other contacts included in the circuit (e.g., if multiple contacts are coupled in parallel in the circuit), and then subtracted from a total impedance to obtain the impedance for a given contact. In another embodiment, a series of multivariable equations can be used to solve for the impedance of each individual contact. Such an implementation is expected to consume more power than others, and accordingly, may in at least some embodiments be selected only when suitable power is available. In another approach, the microprocessor 107 can employ a successive approximation technique by using an initially measured value for one contact to estimate values for other contacts, and then repeating the process as the impedances of circuits with other contacts are identified. In any of the foregoing embodiments, the detector 119 obtains impedance values and/or changes in impedance values which are provided as inputs to other functional elements of the microprocessor 107 that automatically implement the changes described above with reference to FIGS. 2 and 3.

Figure 5A:
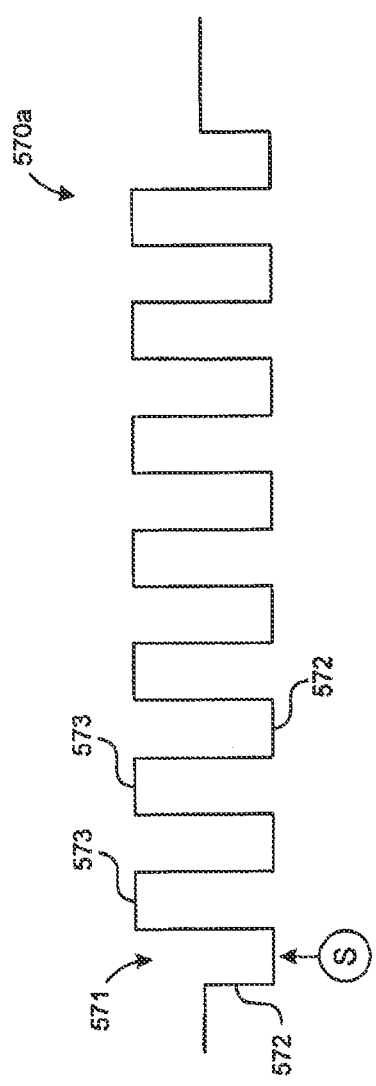
FIGS. 5A and 5B are schematic illustrations of waveforms indicating points at which impedance detection may be performed in accordance with embodiments of the disclosure.

FIG. 5A illustrates a representative waveform 570*a* having multiple pulses 571, each with a cathodic phase 572 and an anodic phase 573 for delivering therapy to the patient. In a particular aspect of this embodiment, the waveform 570*a* can be sampled directly (e.g., at the cathodic phase 572) via the circuit described above with reference to FIG. 4B, to identify circuit impedance. For example, arrow S identifies a suitable sampling point. In particular embodiments, the waveform 570*a* can be sampled at multiple points, and the results analyzed to provide a complex impedance value.

Figure 5B:
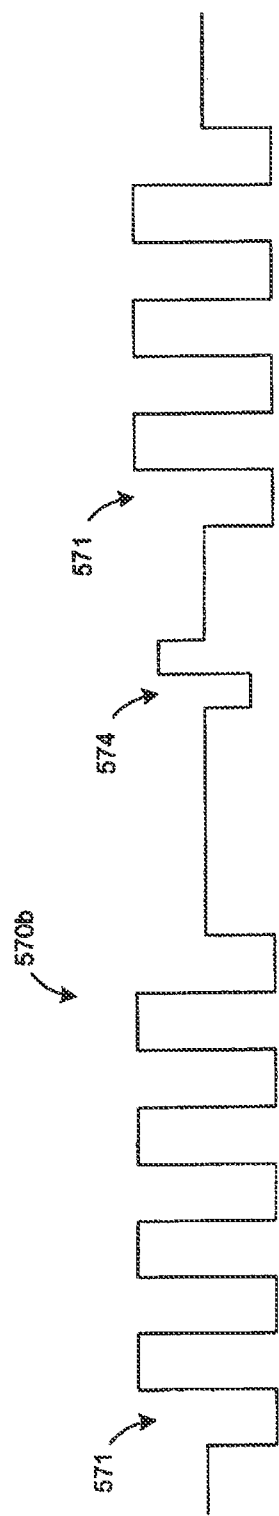

FIG. 5B illustrates another waveform 570*b* having multiple bursts of pulses 571 separated by a quiescent period. In this embodiment, a separate detection pulse 574 can be superimposed on the waveform 570*b* at the quiescent period. The impedance characteristics of the circuit are accordingly determined by analyzing the impedance associated with the detection pulse 574. In still further embodiments, the detection pulse 574 can be applied to a circuit that is not applying therapy at that time, in which case the waveform 570*b* is entirely quiescent except for the presence of the detection pulse 574. In any of these embodiments, the detection pulse 574 is typically provided at subthreshold leads to avoid triggering a motor and/or sensory response in the patient.

In any of the foregoing embodiments, the therapy signal can be applied at frequencies ranging from about 1.5 kHz to about 100 kHz, duty cycles of from about 50% to about 100%, e.g., with the modulation signal on for a period of about 10 milliseconds to about 2 milliseconds, and off for a period of about 1 millisecond to about 1.5 milliseconds. The applied pulses can have a width of from about 30 to 35 microseconds and an amplitude in the range of about 1 mA to about 4 mA. Other representative parameters are included in co-pending U.S. Patent Publication No. US2010/0274314, incorporated herein by reference in its entirety. In other embodiments, these parameters can have different values suitable for providing patient therapy to any of a variety of neural populations to address any of a variety of patient conditions.

Embodiments of the present technology include applying therapy signals in accordance with the above parameters to produce pain relief without associated paresthesia. In addition, the pain reduction effects of the therapy signals can persist for a significant period of time after the signal has ceased (see, e.g., U.S. Patent Publication No. 2012/0172946, incorporated herein by reference in its entirety. Accordingly, the patient may not notice an interrupted or degraded signal for an extended period of time. As discussed above, to prevent a sudden and/or unexpected onset of pain, methods and systems in accordance with the present technology can provide an indication of a fault to the patient and/or the practitioner. Several embodiments in accordance with the present technology can automatically detect an open circuit or a degraded signal by periodically performing an impedance check. For example, in one embodiment, the system 100 can perform an impedance check every minute. In other embodiments, the system 100 can perform an impedance check at other longer or shorter intervals. In particular embodiments for which the therapy signal is used to perform an impedance check, the impedance can be checked on a continuous or almost continuous basis. In any of these embodiments, the fault indication provided by the system can elicit a corrective and/or compensatory response from the patient and/or practitioner and/or the system itself. Suitable responses include, but are not limited to, reconnecting the lead and/or extension to the external programmer, shifting the therapy signal(s) to different contacts of the same signal delivery device (e.g., for a multi-contact signal delivery device) and/or to a different implanted signal delivery device (e.g., if the patient has multiple implanted signal delivery devices), and/or replacing the signal delivery device, the implanted signal generator, and/or the lead extension.

Figure 6:
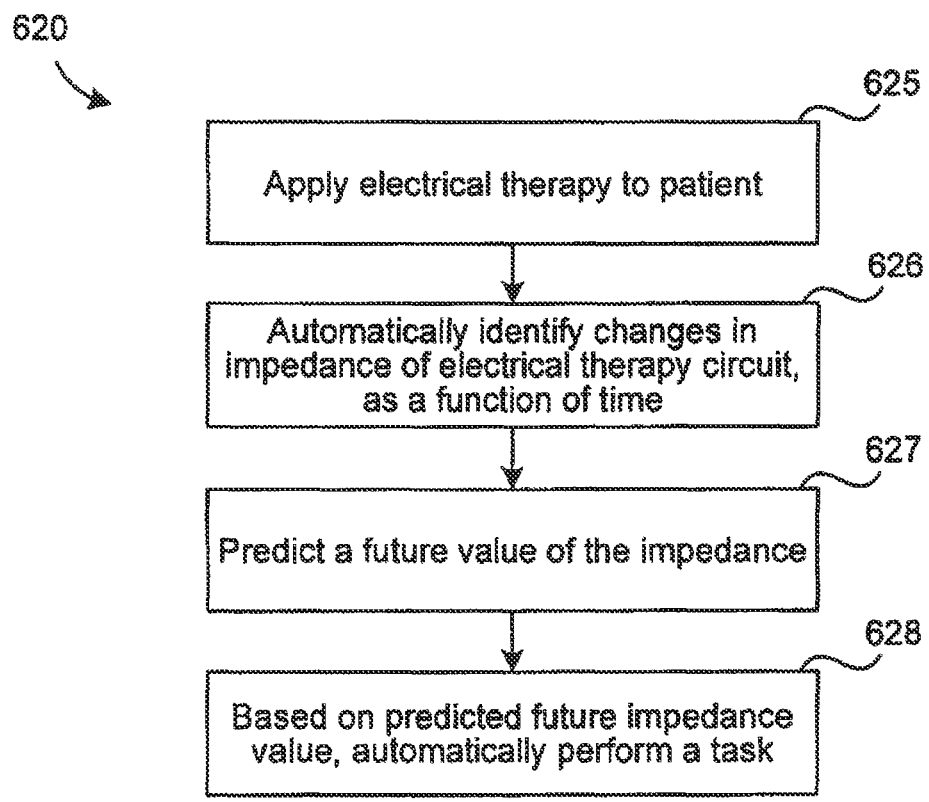
FIG. 6 is a flow diagram illustrating a process for predicting future values of impedance based on impedance trends in accordance with an embodiment of the disclosure.

FIG. 6 is a flow diagram illustrating a process 620 in accordance with another embodiment of the disclosure. Process 620 can include applying electrical therapy to the patient (process portion 625), and automatically identifying changes in the impedance of an electrical circuit via which the therapy is applied, as a function of time (process portion 626). Based on the information obtained in process portion 626, process portion 627 can include predicting a future value of the impedance. For example, the future value can be predicted by a suitable extrapolation technique, including a linear or higher order function, a least-squares curve fit, or other technique. Based on the predicted future value of the impedance, process portion 628 can include automatically performing a task, e.g., without human intervention. Representative tasks can include predicting a lead failure, e.g., if the lead impedance intermittently becomes excessive. In other embodiments, process portion 628 can include predicting excessive impedance such as may result from the formation of scar tissue around a lead, for example, if the impedance exhibits a steady growth. Still another function that may be performed via process portion 628 includes confirming that the impedance trend identified in process portion 626 conforms with an expected trend, for example, an expected trend or schedule resulting from an expected amount of scar tissue growth. In still another embodiment, the task can include updating any of the signal delivery parameters described above, and/or adjusting the compliance values and/or compliance margins, as discussed above. In any of these embodiments, process portion 628 can include notifying the patient and/or practitioner, alone or in combination with any of the foregoing activities.

From the foregoing, it will be appreciated that specific embodiments of the disclosure have been described herein for purposes of illustration, but that various modifications may be made without deviating from the disclosure. For example, while certain aspects of the disclosure were described above in the context of spinal cord modulation to treat chronic pain, similar techniques may be used in other embodiments to identify impedance changes and/or trends for therapy applied to other neural populations and/or for other patient conditions. The signal delivery parameters described above may have other values in other embodiments, for example, lower frequencies than the 1.5 kHz-100 KHz range described above. The detection circuits can have arrangements other than those specifically disclosed herein. The microprocessor can implement responses to the detected impedance changes using any of a variety of suitable programming languages and techniques.

Certain aspects of the foregoing disclosure described in the context of particular embodiments may be combined or eliminated in other embodiments. For example, the process of predicting impedance trends discussed above with reference to FIG. 6 may be combined with the process for adjusting impedance values described above with reference to FIGS. 2 and 3. The impedance values may be tracked in a manner that is coordinated with patient position or activity, as is disclosed in co-pending U.S. Patent Publication No. US2010/0211135, incorporated herein by reference in its entirety. The method of tracking impedance changes as a function of time and predicting future impedance values need not be performed by an implanted portion of the system in some embodiments, and can instead be performed outside the patient. Additional representative therapy devices and methods are disclosed in U.S. Patent Publication 2009/0204173 and U.S. patent application Ser. No. 13/607,617, both of which are incorporated herein by reference. Further, while advantages associated with certain embodiments have been described in the context of those embodiments, other embodiments may also exhibit such advantages, and not all embodiments need necessarily exhibit such advantages to fall within the scope of the present disclosure. The following examples provide further representative embodiments of the presently disclosed technology.

We claim:

1. A method for controlling a patient therapy device, comprising:
   applying a therapeutic, paresthesia-less electrical signal to a target neural population in a patient via a patient modulation system that includes an implantable portion having a signal delivery device;
   detecting a change in an impedance of an electrical circuit that delivers the electrical signal, without the patient sensing a corresponding change in therapy; and
   providing a notification prompting the patient and/or a practitioner to correct or compensate for the change in impedance.

2. The method of claim 1 wherein providing the notification prompting the patient and/or practitioner to correct or compensate for the change in impedance comprises providing the notification prior to the patient experiencing a change in therapy resulting from the change in impedance.

3. The method of claim 1 wherein the notification elicits a corrective or compensatory response.

4. The method of claim 3 wherein the corrective or compensatory response includes:
   changing an active contact applying the electrical signal to the patient;
   changing a number of active contacts used to apply the electrical signal to the patient;
   and/or
   increasing a strength of the electrical signal.

5. The method of claim 3 wherein the electrical signal includes one or more signal delivery parameters, and wherein the corrective or compensatory response includes updating values of one or more of the signal delivery parameters.

6. The method of claim 1 wherein providing the notification comprises:
   generating, via the implantable portion of the patient modulation system, a signal corresponding to the notification; and
   transmitting the signal to a device positioned external to the patient.

7. The method of claim 1 wherein detecting the change in impedance occurs while applying the therapeutic, paresthesia-less electrical signal to the patient.

8. The method of claim 1 wherein applying the therapeutic, paresthesia-less signal includes applying the electrical signal at a frequency in a range from 1.5 kHz to 100 kHz.

9. A method for controlling a patient therapy device, comprising:
   applying a therapeutic, paresthesia-less electrical signal to a target neural population in a patient via a patient modulation system that includes a signal delivery device;
   monitoring an impedance of an electrical circuit that includes the signal delivery device;
   detecting a change in the impedance of the electrical circuit that indicates a fault, before or without the patient sensing a change in therapy resulting from the fault; and
   in response to detecting the change in the impedance, providing a notification prompting the patient and/or a practitioner to correct or compensate for the fault.

10. The method of claim 9 wherein providing the notification prompting the patient and/or the practitioner to correct or compensate for the fault comprises providing the notification prior to the patient experiencing a change in therapy resulting from the fault.

11. The method of claim 9 wherein the notification elicits a corrective or compensatory response.

12. The method of claim 11 wherein the corrective or compensatory response includes:
   changing an active contact applying the electrical signal to the patient;
   changing a number of active contacts used to apply the electrical signal to the patient;
   and/or
   increasing a strength of the electrical signal.

13. The method of claim 11 wherein the electrical signal includes one or more signal delivery parameters, and wherein the corrective or compensatory response includes updating values of one or more of the signal delivery parameters.

14. The method of claim 9 wherein providing the notification comprises:
   generating, via the implantable portion of the patient modulation system, a signal corresponding to the notification; and
   transmitting the signal to a device positioned external to the patient.

15. The method of claim 9 wherein monitoring the impedance of the electrical circuit includes monitoring the impedance of the electrical circuit on a pre-set periodic basis.

16. A patient therapy system, comprising:
   a patient-implantable portion that includes a signal generator and a signal delivery device having an electrical contact positioned to be in electrical communication with a neural population in a patient when implanted, wherein the signal generator produces an electrical signal that provides pain relief;
   an impedance detector carried by the patient-implantable portion, the impedance detector being operatively coupled to an electrical circuit that includes the electrical contact to detect an impedance of the electrical circuit; and a processor carried by the patient-implantable portion, the processor having a computer-readable medium programmed with instructions that, when executed, perform a process that includes— monitoring the impedance of the electrical circuit;

receiving an indication from the impedance detector corresponding to a change in the impedance of the electrical circuit before or without the patient sensing a corresponding change in therapy; and after receiving the indication, generating a notification prompting the patient and/or a practitioner to correct or compensate for the change in impedance.

17. The system of claim 16 wherein the process further includes transmitting the notification to an external device.

18. The system of claim 17 wherein the notification is transmitted to the external device prior to the patient experiencing a change in therapy resulting from the change in impedance.

19. The system of claim 16 wherein the notification elicits a corrective response.

20. The system of claim 16 wherein the change in impedance results from a fault, and wherein the processor is configured to determine if the fault has been corrected.

* * * * *